US007581846B2

(12) United States Patent
Hayman et al.

(10) Patent No.: US 7,581,846 B2
(45) Date of Patent: Sep. 1, 2009

(54) DENTAL LIGHT DEVICES HAVING AN IMPROVED HEAT SINK

(75) Inventors: Robert Hayman, Los Angeles, CA (US); Younes Shabany, San Jose, CA (US); Eric P. Rose, Tarzana, CA (US)

(73) Assignee: Discus Dental, LLC, Culver City, CA (US)

( * ) Notice: Subject to any disclaimer, the term of this patent is extended or adjusted under 35 U.S.C. 154(b) by 0 days.

(21) Appl. No.: 11/173,274

(22) Filed: Jun. 30, 2005

(65) Prior Publication Data

US 2006/0013014 A1    Jan. 19, 2006

Related U.S. Application Data

(60) Provisional application No. 60/594,327, filed on Mar. 30, 2005, provisional application No. 60/594,297, filed on Mar. 25, 2005, provisional application No. 60/664,696, filed on Mar. 22, 2005, provisional application No. 60/658,517, filed on Mar. 3, 2005, provisional application No. 60/647,580, filed on Jan. 26, 2005, provisional application No. 60/647,612, filed on Jan. 26, 2005, provisional application No. 60/641,469, filed on Jan. 4, 2005, provisional application No. 60/641,468, filed on Jan. 4, 2005, provisional application No. 60/631,267, filed on Nov. 26, 2004, provisional application No. 60/604,577, filed on Aug. 25, 2004, provisional application No. 60/585,224, filed on Jul. 2, 2004.

(51) Int. Cl.
*B25B 23/18* (2006.01)

(52) U.S. Cl. ............... 362/119; 362/109; 362/294; 362/373; 250/504 H; 433/229

(58) Field of Classification Search ............... 362/572, 362/273, 119, 109, 230, 294; 433/29, 215, 433/226, 229; 250/504 H
See application file for complete search history.

(56) References Cited

U.S. PATENT DOCUMENTS

| 4,615,679 | A | 10/1986 | Wyatt |
| 4,632,865 | A | 12/1986 | Tzur |
| 4,825,939 | A | 5/1989 | Salyer et al. |
| 5,420,768 | A | 5/1995 | Kennedy |
| 5,634,711 | A | 6/1997 | Kennedy |
| 5,722,482 | A | 3/1998 | Buckley |
| 5,851,661 | A | 12/1998 | Werenicz et al. |
| 6,077,073 | A | 6/2000 | Jacob |
| 6,159,005 | A | 12/2000 | Herold |
| 6,200,134 | B1 | 3/2001 | Kovac |

(Continued)

FOREIGN PATENT DOCUMENTS

WO    WO 99-16136 A1    4/1999

*Primary Examiner*—Jacob Y Choi

(57) ABSTRACT

The present invention relates to a heat sink material that can more efficiently remove or divert heat from a light source or sources with a given weight of heat sink material when compare to a heat sink made of a solid block of thermally conductive material such as metal. It further relates to a heat sink that can more efficiently remove or divert heat from a curing light device when a reduced weight of heat sink material is used. The inventive heat sink has at least one suitable phase change material including organic materials, inorganic materials and combinations thereof. These materials can undergo substantially reversible phase changes, and can typically go through a large, if not an infinite number of cycles without losing their effectiveness.

55 Claims, 6 Drawing Sheets

U.S. PATENT DOCUMENTS

| | | | |
|---|---|---|---|
| 6,207,738 B1 | 3/2001 | Zuckerman et al. |
| 6,274,924 B1 | 8/2001 | Carey |
| 6,318,996 B1 | 11/2001 | Melikechi |
| 6,331,111 B1 | 12/2001 | Cao |
| 6,419,483 B1 | 7/2002 | Adam et al. |
| 6,432,547 B1 | 8/2002 | Kroll et al. |
| 6,439,888 B1 | 8/2002 | Boutoussov et al. |
| 6,468,077 B1 | 10/2002 | Melikechi et al. |
| 6,498,355 B1 | 12/2002 | Harrah et al. |
| 6,514,075 B1 | 2/2003 | Jacob |
| 6,517,218 B2 | 2/2003 | Hochstein |
| 6,616,447 B1 | 9/2003 | Rizoiu et al. |
| 6,692,251 B1 | 2/2004 | Logan et al. |
| 6,692,252 B2 | 2/2004 | Scott |
| 6,695,614 B2 | 2/2004 | Plank |
| 6,702,576 B2 | 3/2004 | Fischer et al. |
| 6,703,128 B2 | 3/2004 | Myers et al. |
| 6,709,128 B2 * | 3/2004 | Gordon et al. ............... 362/119 |
| 6,719,558 B2 | 4/2004 | Cao |
| 6,719,559 B2 | 4/2004 | Cao |
| 6,724,522 B2 | 4/2004 | Hartung |
| 6,755,648 B2 | 6/2004 | Cao |
| 6,755,649 B2 | 6/2004 | Cao |
| 6,759,476 B1 | 7/2004 | Hayes |
| 6,780,010 B2 | 8/2004 | Cao |
| 6,780,505 B1 | 8/2004 | Klett et al. |
| 6,783,362 B2 | 8/2004 | Cao |
| 6,793,490 B2 | 9/2004 | Bianchetti et al. |
| 6,793,844 B2 | 9/2004 | Hayes |
| 6,799,967 B2 | 10/2004 | Cao |
| 6,809,740 B1 | 10/2004 | Weed |
| 6,824,294 B2 | 11/2004 | Cao |
| 6,835,064 B2 | 12/2004 | Burtscher et al. |
| 6,843,967 B2 | 1/2005 | Clark |
| 6,848,500 B1 | 2/2005 | Langari |
| 6,890,175 B2 | 5/2005 | Fischer et al. |
| 6,926,524 B2 | 8/2005 | Cao |
| 6,929,472 B2 | 8/2005 | Cao |
| 6,932,600 B2 | 8/2005 | Cao |
| 6,940,659 B2 | 9/2005 | McLean et al. |
| 6,971,876 B2 | 12/2005 | Cao |
| 6,988,890 B2 | 1/2006 | Cao |
| 6,988,891 B2 | 1/2006 | Cao |
| 2001/0046652 A1 | 11/2001 | Ostler |
| 2002/0115037 A1 | 8/2002 | Cao |
| 2002/0167283 A1 | 11/2002 | Cao |
| 2002/0167605 A1 | 11/2002 | Akimoto |
| 2002/0168603 A1 | 11/2002 | Cao |
| 2002/0168604 A1 | 11/2002 | Cao |
| 2002/0168607 A1 | 11/2002 | Cao |
| 2002/0172912 A1 | 11/2002 | Cao |
| 2002/0172914 A1 | 11/2002 | Cao |
| 2002/0172915 A1 | 11/2002 | Cao |
| 2002/0172916 A1 | 11/2002 | Cao |
| 2002/0172917 A1 | 11/2002 | Cao |
| 2002/0175628 A1 | 11/2002 | Cao |
| 2002/0177095 A1 | 11/2002 | Cao |
| 2002/0177096 A1 | 11/2002 | Cao |
| 2002/0177099 A1 | 11/2002 | Cao |
| 2002/0180368 A1 | 12/2002 | Cao |
| 2002/0181947 A1 | 12/2002 | Cao |
| 2002/0190659 A1 | 12/2002 | Cao |
| 2002/0190660 A1 | 12/2002 | Cao |
| 2002/0197582 A1 | 12/2002 | Cao |
| 2003/0001507 A1 | 1/2003 | Cao |
| 2003/0036031 A1 * | 2/2003 | Lieb et al. ..................... 433/29 |
| 2003/0215766 A1 * | 11/2003 | Fischer et al. ................. 433/29 |
| 2004/0043351 A1 | 3/2004 | Logan et al. |
| 2004/0101802 A1 | 5/2004 | Scott |
| 2004/0120162 A1 * | 6/2004 | Tsimerman et al. ......... 362/573 |
| 2005/0142514 A1 * | 6/2005 | Scott ........................... 433/29 |
| 2005/0158687 A1 * | 7/2005 | Dahm ........................ 433/29 |
| 2005/0182561 A1 | 8/2005 | Yamada |

* cited by examiner

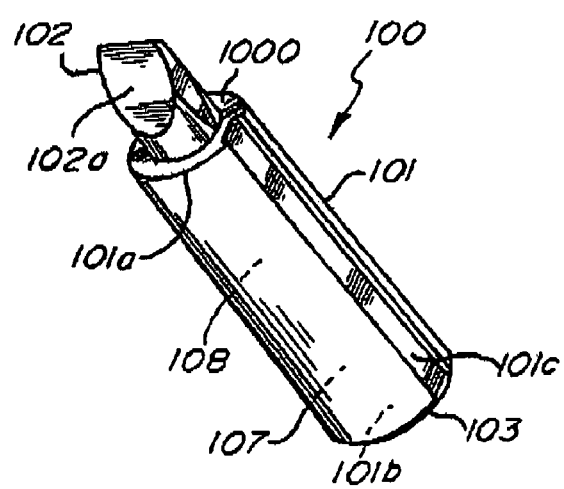
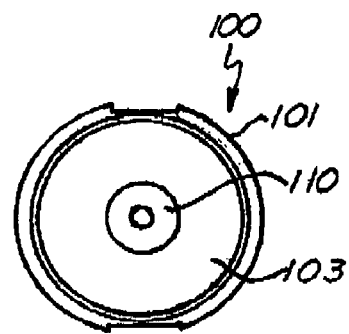
Fig.1.
Fig.1a.
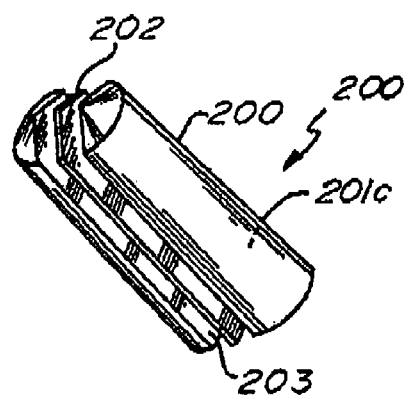
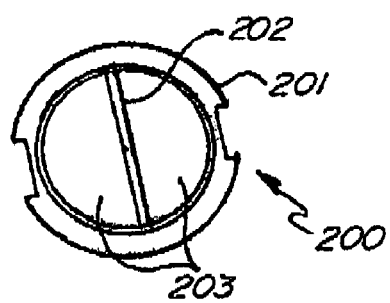
Fig.2.
Fig.2a.

DENTAL LIGHT DEVICES HAVING AN IMPROVED HEAT SINK

CROSS-REFERENCE TO RELATED APPLICATIONS

This application claims the benefit of U.S. provisional application Ser. Nos. 60/585,224, filed Jul. 2, 2004, entitled "Dental Light Devices With Phase Change Heat Sink"; 60/658,517, filed Mar. 3, 2005, entitled "Apparatus and Method For Radiation Spectrum Shifting in Dentistry Application"; 60/641,469, filed Jan. 4, 2005, entitled "Lamp For Dentistry Applications"; 60/647,580, filed Jan. 26, 2005, entitled "Light Guide For Dental Whitening Lamp"; 60/641,468, filed Jan. 4, 2005, entitled "Light Guide For A Dental Whitening Lamp"; 60/647,612, filed Jan. 26, 2005, entitled "Light Path Apparatus For A Dental Lamp"; 60/604,577, filed Aug. 25, 2004, entitled "Lip Retractors"; 60/594,297, filed Mar. 25, 2005, entitled "Curing Light Having A Detachable Tip"; 60/631,267, filed Nov. 26, 2004, entitled "Curing Light Having A Reflector"; 60/594,327, filed on Mar. 30, 2005, entitled, "Curing Light"; and 60/664,696, filed Mar. 22, 2005, entitled "Curing Light Having A Detachable Tip"; the contents of all of which are hereby incorporated by reference.

The present application includes claims that may be related to the claims of co-pending U.S. patent applications, Ser. No. 11/173,839, to be concurrently filed, entitled "Illumination System for Dentistry Applications"; Ser. No. 11/173,709, to be concurrently filed, entitled "Voice Alert in Dentistry Applications"; Ser. No. 11,173,297, to be concurrently filed, entitled "Retracting Devices"; Ser. No. 11/173,734, to be concurrently filed, entitled "Light Guide for Dentistry Applications"; and Ser. No. 11/173,731 to be concurrently filed, entitled "Support System for Dentistry"; the contents of all of which are hereby incorporated by reference.

FIELD OF THE INVENTION

The present invention relates to any device suitable for photocuring, or photobleaching in general. Particularly, it relates a photocuring, or photobleaching device suitable for curing dental composites or acting on a whitening gel, respectively, having an improved heat sink.

BACKGROUND OF THE INVENTION

Composite resin fillings have become the standard for filling cavities in dentistry today. These composite fillings use resins that must be cured after application. Handheld curing lights have been extensively used for this curing purpose. The lights can be held in close proximity to the composite resin materials residing in patients' mouths. The exposure times required for curing the composite materials depend on the types of composite resins used. Thus, the lighter the handhelds, the easier it is for the dental professionals who have to hold such devices in place to effect curing.

At the same time teeth bleaching is also routinely done by dental professionals. One type of bleaching composition is photoactivated. During photobleaching, a bleaching light is utilized.

Heat generated by any curing lights during operation can be problematic. Industry safety standards dictate that the external surface temperature of the curing light cannot exceed 50° C. Additionally, the duration or run time before the curing light overheats and shuts off is dependent on how much and how quickly heat can be removed from the curing light. This same kind of problem is also encountered in photobleaching lights. Therefore, any efficient way of heat removal is desirable for both curing and photobleaching lights.

Various ways have been attempted to remove the heat generated. One common way is through the use of metal heat sinks, such as blocks of copper, and cooling fans contained within the curing or photobleaching light. Some devices use a combination of heat sinks and cooling fans to facilitate removal.

Blocks of metal can be efficient, but they can also add significant weight to any hand held curing light. The added weight can in turn contribute to increased fatigue of the dental professional using the curing light. When a fan is also used in the same curing light, it adds additional weight, can be noisy and can contribute to reduced battery life and reliability of the device. The noise also adds to the anxiety of the patients who are often reluctant and fearful of dental procedures.

Although devices used for photobleaching and some curing lights are supported during use so that any added weight is not as problematic as a portable curing light device, a more efficient heat sink can also be beneficial, contributing to the design of a more compact device. Therefore, there remains a need for a device that will more efficiently divert or remove heat from the light source without additional weight.

SUMMARY OF THE INVENTION

The present invention relates to a heat sink material that can more efficiently remove or divert heat from a light source or sources with a given weight of heat sink material when compare to a heat sink made of a solid block of thermally conductive material such as metal.

The present invention further relates to a heat sink that can more efficiently remove or divert heat from a curing light device when a reduced weight of heat sink material is used.

The present invention includes a heat sink having at least one suitable phase change material including organic materials, inorganic materials and combinations thereof. These materials can undergo substantially reversible phase changes, and can typically go through a large, if not an infinite number of cycles without losing their effectiveness.

In one embodiment, a rechargeable dental curing light including at least one heat sink having at least one phase change material is disclosed. The heat sink includes a block of thermally conductive material such as metal having a bore or void space which is at least partially filled with a phase change material.

In another embodiment, a bleaching light including at least one heat sink having at least one phase change material is disclosed. The heat sink includes a block of thermally conductive material such as a metal having a bore or void space which is at least partially filled with a phase change material.

The heat sink of the present invention may be constructed by hollowing out a thermally conductive material, such as metal, and at least partially filling the void with at least one phase change material prior to capping it to secure the phase change material inside, such that the at least one phase change material is substantially contained or surrounded by a thermally conductive material such as a metal normally used in the construction of a conventional metal heat sink.

Alternatively, the heat sink can be cast or machined with thermally conductive material such as metal walls surrounding a bore or void. The bore or void is partially filled with at least one phase change material prior to capping it to secure the material inside.

In one embodiment, the inventive heat sink may be used by itself. In another embodiment, it may be used in addition to a fan, in conjunction with a conventional metal block heat sink or combinations thereof.

The inventive heat sink may be installed into a dental curing light or bleaching light in the same manner a conventional a metal block heat sink is installed, such as by attaching it to the heat source, i.e., the light source, which may be a gas-filled arc light such as a halogen source, a Xenon light, a metal halide, a fluorescent light source semiconductor light emitting devices, laser emitting light source, light emitting chips such as a light-emitting diode (LED), a solid-state LED, an LED array, or combinations thereof, or by attaching it to another heat sink.

BRIEF DESCRIPTION OF THE DRAWINGS

FIG. 1 shows a perspective view of an embodiment of a heat sink of the present invention;

FIG. 1a shows a perspective bottom view of the embodiment of the heat sink of FIG. 1;

FIG. 2 shows an explode view of another embodiment of a heat sink of the present invention;

FIG. 2a shows a perspective bottom view of the embodiment of FIG. 2 without a cap;

DETAILED DESCRIPTION OF THE INVENTION

Figure 3:
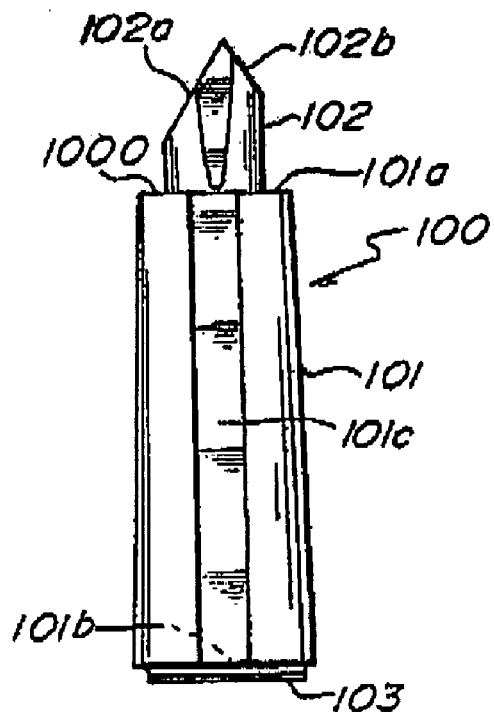
FIG. 3 shows a side profile view of the embodiment of the heat sink of FIG. 1 of the present invention.

The detailed description set forth below is intended as a description of the presently exemplified embodiments of the present invention and is not intended to represent the only forms in which the present invention may be prepared or utilized. The description sets forth the features and the steps for practicing the present invention and is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

A curing light system useful for curing light activated composite materials or a light system useful for whitening teeth typically comprises a light module housed in an encasement or housing.

Using a phase change material enclosed inside a substantially hollow, thermally conductive material such as a metal instead of a conventional solid metal heat sink can decrease the weight of the curing light and increase the time the heat sink takes to reach the "shut off" temperature, as it is called in the dental curing light industry. The period prior to reaching the shut off temperature is called the "run time". Increasing the "run time", i.e., the time when the light can remain on, increases the time when a dentist can perform his curing procedure.

Phase change materials may include organic materials, such as paraffin waxes, 2,2-dimethyl-n-docosane ($C_{24}H_{50}$), trimyristin, (($C_{13}H_{27}COO)_3C_3H_3$), 1,3-methyl pentacosane ($C_{26}H_{54}$), other polyethylene waxes, ethylene-bis-stearamide, N,N-ethylene-bis-stearamide, or similar, which may be used alone or in mixtures thereof. Inorganic materials such as hydrated salts including sodium hydrogen phosphate dodecahydrate ($Na_2HPO_4.12H_2O$), sodium sulfate decahydrate ($Na_2SO_4.10H_2O$), ferric chloride hexahydrate ($FeCl_3.6H_2O$), TH29 (a hydrated salt having a melting temperature of 29° C., available from TEAP Energy of Wangara, Australia) or similar, which may be used alone or in mixtures thereof. Other inorganic materials may include metallic alloys, such as Ostalloy 117 or UM47 (available from Umicore Electro-Optic Materials) is also contemplated. Exemplary materials are solids at ambient temperature, having melting points between about 30° C. and about 50° C., more for example, between about 35° C. and about 45° C. Also, the exemplary materials may have a high specific heat, for example, at least about 1.7, more for example, at least about 1.9, when they are in the state at ambient temperature. In addition, the phase change materials may, for example, have a specific heat of at least about 1.5, more for example, at least about 1.6, when they are in the state at the elevated temperatures.

Some of the phase change materials mentioned above may be recyclable in that they may undergo phase changes for an almost infinite number of times. Others may be more endothermic agents and thus may have a limited life cycle unless handled under a controlled environment. These endothermic agents may lose their effectiveness as a phase change material even when handled under a controlled environment.

For some metallic alloys, though their heat of fusion may be low, they may be better thermal conductors than other phase change materials with higher heat of fusion. Thus a mixture of a metallic alloy with one or more of the other inorganic or organic phase change materials may be used to increase heat conductivity within the phase change material.

Thermal conductivity of the materials is a factor used in determining the rate of heat dissipation. For example, the thermal conductivity of the phase change material is at least about 0.5 W/m° C. in the state at ambient temperature, and at least about 0.45 W/m° C. in the state at elevated temperature.

In general, the phase change material may be contained inside a thermally conductive housing or casing, such as a metal housing. The housing defines a bore, which may be of any shape, but is for example, of a circular or a rectangular cross-section. The metal casing or wall of the bore acts to contain the phase change material, and to also aid in conducting heat to and away from the phase change material. The thinner the wall, the more phase change material can be present for a given size of the heat sink, and the less it contributes to the weight of the curing light. However, the thinner the wall, the less efficient the wall may be in conducting heat away from the phase change material and the longer it will take to return the phase change material to ambient temperature and its original state, so that it can function as a heat sink again. For example, a wall thickness typically ranges from about 1 mm to about 2.5 mm, more for example, from about 1 mm to about 1.5 mm for balance of properties.

Also, the housing may be constructed to have a large surface area. For example, a structure having fins or other features on its outside surface may serve to increase the surface area for heat conduction or convection. A spherical structure may therefore be less desirable. Such fins or other surface area increasing features may also be incorporated into the bore to increase the contact area between the thermally conductive casing and the phase change material, thus permitting faster and more efficient transfer of heat between the thermally conductive casing and the phase change material. Also, as noted above, a mixture of organic or inorganic phase change material with a metallic alloy may also increase the efficiency of heat transfer inside the phase change material.

It may also be desirable for the thermally conductive casing to be in good thermal contact for heat transfer from the light source. This may be accomplished with a smooth, thermally conductive surface with a large area of contact. Also, thermal coupling may be achieved with thermally conductive interface materials such as thermal epoxy or other thermally conductive adhesives. Interface materials that are electrically insulating are also useful in isolating the light source from the heat sink in an electrical sense without losing thermal conductivity.

Some phase change material may also have a high latent heat of fusion to store significant amounts of heat energy, as noted above. A latent heat of fusion of at least about 30 kJ/kg, is desirable, with a latent heat of fusion of at least about 200 kJ/kg being more desirable.

Figure 5:
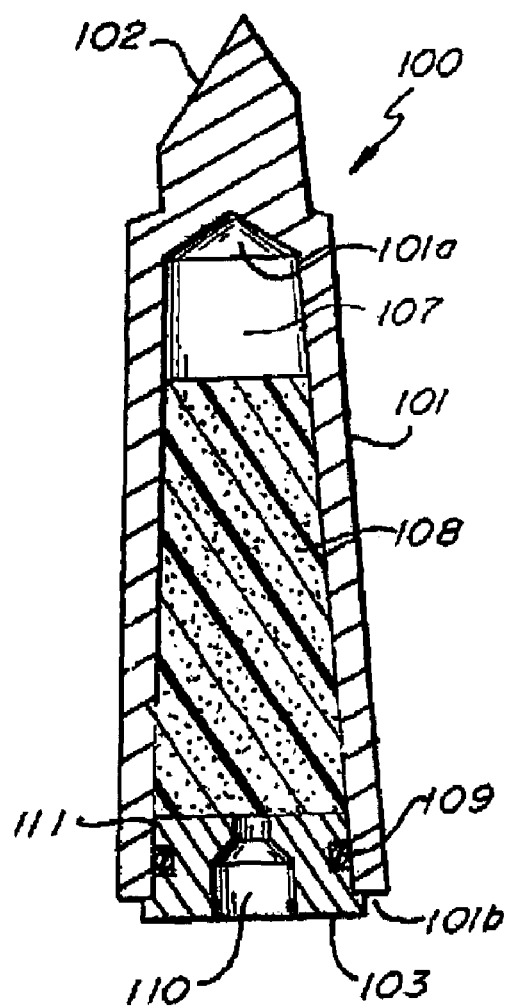
FIG. 5 shows a cross-sectional view of the heat sink of FIG. 1.

In one embodiment, a heat sink 100 may have a substantially cylindrical form, as shown in FIG. 1. The housing 101 may be made of copper, aluminum, or any other relatively light weight metal having good thermal conductivity. The housing includes a substantially hollow interior 107, and is partially filled with a solid phase change material 108, such as sodium hydrogen phosphate dodecahydrate ($Na_2HPO_4.12H_2O$) or any of the materials mentioned above, to at least about 50% by volume of the hollow interior 107, as shown in FIG. 5. Depending on the vapor pressure of the phase change material chosen, the phase change material may be present up to about 80% by volume of the capacity of the hollow interior 107. One end of the housing 101 is closed and the closed end is shown as 101a. The other end of the housing 101 is open, to facilitate filling of the heat sink with the phase change material. The open end 101b, as is shown also in FIG. 5, may be covered with a capping device 103, which may be made of the same material as the rest of the heat sink housing. The heat sink may also include an interface feature 102 for contact with at least one heat generating source, such as a light source.

In the embodiment as shown, the interface feature 102 may be integrally formed with the substantially cylindrical housing if the housing is formed by molding. It may also be machined, if the housing is made by machining.

In one embodiment, the interface feature 102 includes a substantially flat surface 102a for providing a mounting surface and a good thermal interface with a heat generating source, for example, a light source such as an LED. The flat surface 102a is exemplified here as a sloping surface, making an angle with the top portion of the closed end 101a of the housing 101. The interface feature may be of the same diameter as the diameter of the closed end of the housing 101, or it may be of a smaller diameter, leaving at least one shoulder portion 1000. In another embodiment, the interface feature 102 may be of other shapes and dimensions, as long as these other shapes also provide mounting surface or surfaces for light source or sources.

The outside surface of the housing 101 may be constructed with at least one valley or channel 101c, running substantially the length of the outside surface of the housing 101. The valley or channel 101c serves as a place for positioning wiring components for connecting to a light source or sources. The valley or channel may be of a uniform dimension along the length of the housing 101 or may be of irregular width. The valley 101c may also be smooth or rough. As exemplified, the housing 101 includes two parallel channels or valleys, approximately directly opposite each other. In addition to serving as a place for wiring, the valleys 101c also add to the surface area of the heat sink as well as serving to lighten the weight of the heat sink.

Figure 4:
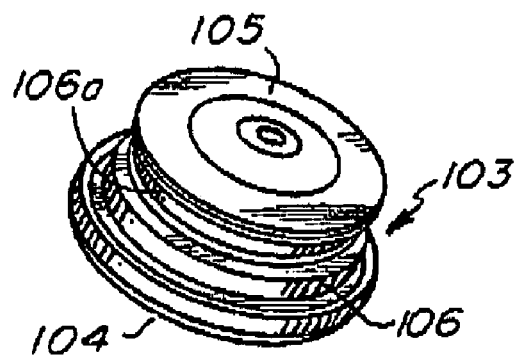
FIG. 4 shows a perspective view of a cap of an embodiment of the heat sink of FIG. 1.

FIG. 1a shows a perspective bottom view of the embodiment of the heat sink in FIG. 1, where the open end is closed by means of a capping device 103, which may be in the shape of a simple cap, or of a more complicated construction, as shown in FIG. 4, described below in more detail.

As exemplified, the capping device 103 is shaped to be fitted inside the open end 101b of the housing 101. The capping device includes a channel or dent 110, adapted for positioning a thermistor or other thermal sensors. The capping device 103 may be held in place inside the open end 101b of the housing by a number of ways. For example, it may be held in place by at least one formation 111, as shown in FIG. 5, adapted for compression fitting the circumference of the capping device against the inside wall of the housing 101, as described in more detailed below.

FIG. 2 shows an exploded perspective view of another embodiment of a heat sink of the present invention. A heat sink 200 includes a substantially cylindrical housing exterior 201, a substantially hollow interior 201c and a blade-like divider 202 disposed within its housing 201. The blade-like divider 202 may run substantially the length of the interior 201c of the housing 201, or it may be of any other length.

The housing 201 may be made of the same thermal conductive material, as noted above. In one embodiment, the blade-like divider 202 may be made of the same material as the housing 201. In another embodiment, the blade-like divider may be made of a different thermal conductive material as the housing 201.

In the exemplified embodiment, the blade-like divider 202 serves to partition a hollow interior 203, as is shown in FIG. 2a. The blade-like divider, like the valley or channel on the outside of the housing, as shown in FIG. 1, may also serve to increase the surface area of contact between a thermally conductive material and the phase change material for more efficient heat conduction, as discussed above and also below. In another embodiment, as noted above, a metallic alloy such as those mentioned above may be mixed with one or more of the other inorganic or organic phase change materials may be used to increase heat conductivity within the phase change material.

A capping device 203 may be fitted into the open end of the housing 201, as is described above, to contain a phase change material.

FIG. 3 shows a side profile view of the heat sink 100 of FIG. 1. The interface feature 102 shows here has two substantially flat surfaces of unequal sizes, a larger surface 102a and a smaller surface 102b, each adapted for providing a mounting surface and a good thermal interface with a heat generating source, if desired.

As shown in FIG. 3, the interface feature 102 is of a smaller diameter as the diameter of the closed end of the housing 101, resulting in shoulder-like portion 1000 protruding from beneath the interface feature 102.

FIG. 4 shows a perspective view of the exterior of a capping device 103, adapted for fitting into a heat sink, as shown in FIGS. 1, 2, 6 and 7. The end portion 105 is adapted to be inserted into the hollow interior 107 of a heat sink, such as shown in FIG. 1, and the second end portion 104 is exposed on the outside of the heat sink 100. A circumferential groove 106a may be included in the vertical wall section 106. This groove is adapted to accommodate an o-ring, a gasket, or other sealing features to provide a air and/or moisture tight seal.

Figure 4A:
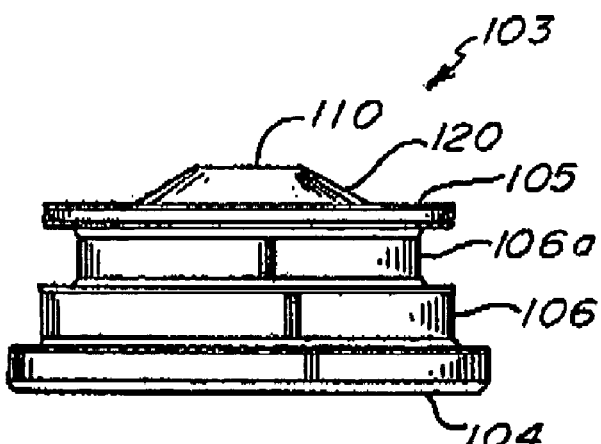
FIG. 4a shows a side view of the embodiment of FIG. 4.

FIG. 4a shows a side view of the capping device 103 exemplified in FIG. 4. The capping device, as shown, includes a channel or dent 110, adapted for positioning a thermistor or other thermal sensors. The dent 110 may be present in a raised portion or mound 120 of the capping device 103. The mound 120 is of a smaller diameter as the rest of the capping device.

As noted above, the capping device 103 may be held in place inside the open end 101b of the housing by a number of ways. In the example as shown in FIG. 5, it is held in place by at least one formation 111, adapted for compression fitting the larger circumference of the end portion 105 of the capping device 103 against the inside wall of the housing 101. A circumferential groove 106a is shown here as having a substantial vertical portion having a reduced diameter. The groove 106a may be molded or machined into the capping device. As noted, this groove is adapted to fit an o-ring, a gasket or other sealing features for sealing the open end of the housing.

The bottom or exposed end 104 of the capping device 103 has a substantially equal diameter or dimension as the outside diameter or dimension as the open end of the housing 101, so that the capping device may be flush with the outside vertical wall of the housing 101. In another embodiment, the diameter of the bottom end 104 of the capping device 103 may be of a larger diameter or dimension as the open end of the housing 101, so that the capping device protrudes from the side of the heat sink to facilitate removal of the capping device 103, if desired.

Figure 4B:
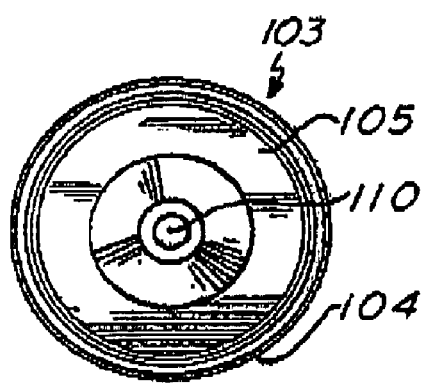
FIG. 4b shows a top view of the embodiment of the cap of FIG. 4.

FIG. 4b shows a top view of the capping device 103 of FIG. 4. As exemplified in this view, the larger diameter of the bottom end 104 than that of the vertical wall section 106 is clearly shown.

Figure 4C:
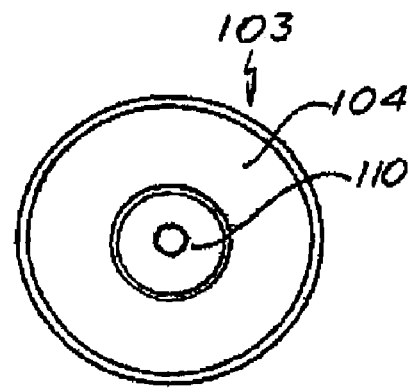
FIG. 4c shows a bottom view of the embodiment of the cap of FIG. 4.

FIG. 4c shows the bottom view of the capping device 103 of FIG. 4, where the depression 110, adapted for holding a thermistor or other thermal sensors, is clearly shown. The depression as shown, has a circular cross-section, but nay other shape may be suitable.

FIG. 5 shows a cross-sectional view of a heat sink 100 of the present invention. The hollow interior 107 includes an open end 101b, which is shown to be capped with a capping device 103, and a closed end 101a. The hollow interior 107 is shown to be substantially filled with a solid phase change material 108, which may include any of the materials described before. The capping device 103 is shown in place, sealing the hollow interior 107 by means of an o-ring 109. The capping device 103 may be held in place by at least one formation 111, adapted for compression fitting the circumference 106 (as shown in FIG. 4a) of the capping device against the inside wall of the housing 101. The cap may also include a channel 110, adapted, for example, to house a thermistor or other thermal sensors. The thermistor or other thermal sensors may be fixed to the channel with a thermally conductive adhesive, such as a structural or permanent adhesive, or a reactive adhesive, for example, an epoxy, a silicone adhesive, a contact cement, or a cyanoacrylate based adhesive, an acrylic-based, a polyurethane-based, a polyamide-based, a styrene copolymer-based, a polyolefin-based or similar, to allow the sensor to provide temperature information to a curing light control system to keep the curing light from becoming too hot to handle or to be over-heated.

In some embodiments, the capping device 103 may also be sealed to an open end of the housing using a structural adhesive, such as those mentioned above in connection with the thermistor. The adhesive seals any pin holes that may exist. In other embodiments, pin holes or vent holes may be desirable to allow gas to escape. To minimize any liquid phase change material from escaping, a vapor impermeable/moisture permeable layer or film may be used to cover the holes.

In some embodiments, the heat sink includes a well and an LED or laser diode chip or chips may be mounted in the well. Light emitted from the side(s) of the LED or laser diode chip or chips may be reflected off the walls of the well to travel in a desired direction. In other embodiments, the well may be deep, as shown in FIG. 6 below.

Figure 6:
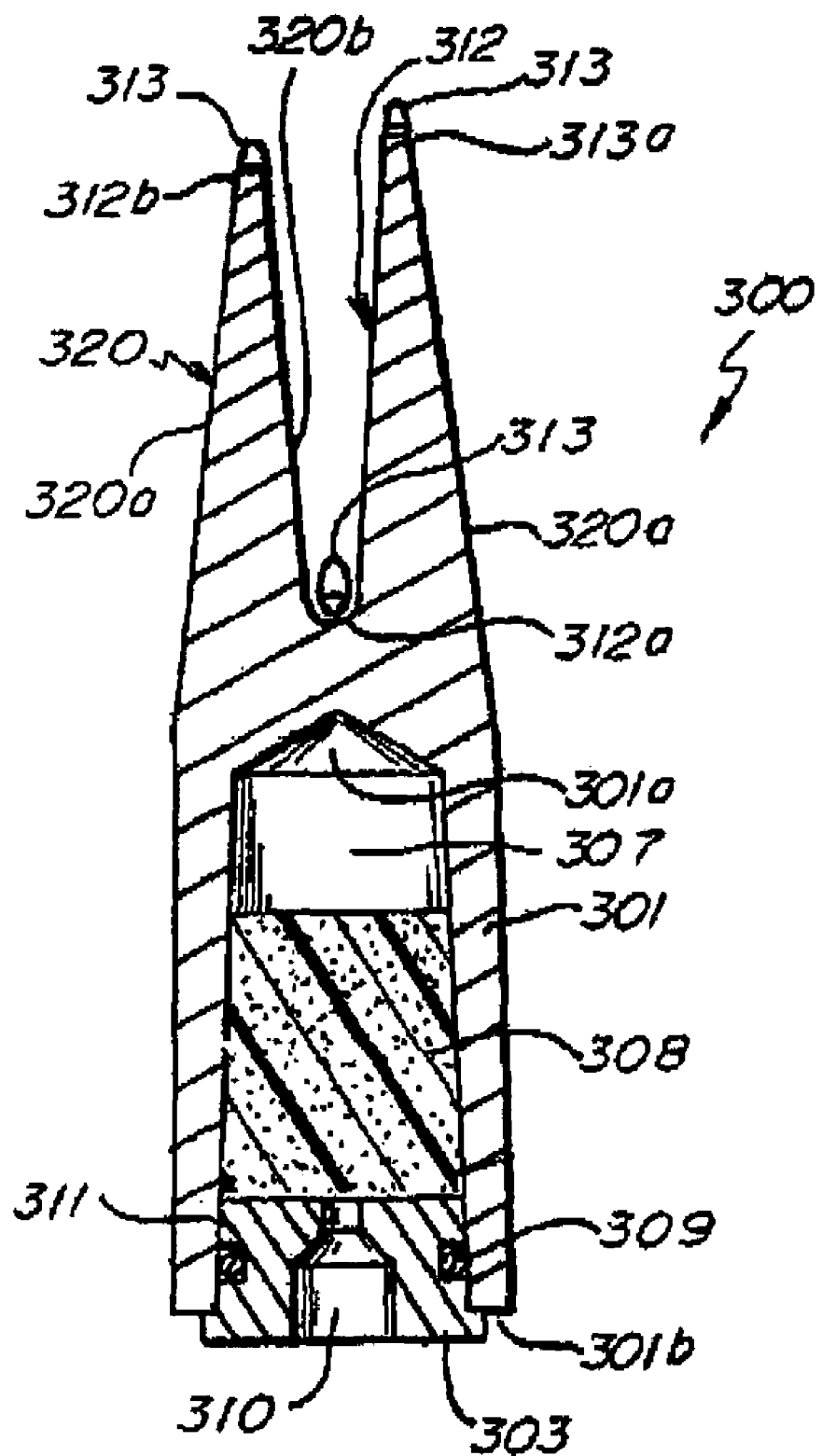
FIG. 6 shows a cross-sectional view of another embodiment of a heat sink of the present invention.

FIG. 6 shows a cross-sectional view of another embodiment of a heat sink 300 of the current invention. In this embodiment, the housing 301 includes a well 312 in place of a protruding feature, such as an interface feature, as shown above. The exemplified embodiment shows an elongated or substantially cylindrical heat sink 300, except that it has a curved structure, for example, a well or depression 312. The well 312 may be deep, having side walls 320 with the proximal portion 312b being at the top of the well and the distal portion 312a at the bottom of the well, adapted for positioning at least a light source such as an LED or LED array 313 at either its distal end 312a or the proximal portion 312b of the well or depression 312, to diffuse the concentration of heat generation.

The proximal portion of the well 312 may include at least two mounting platforms 313a, located, for example, approximately opposite each other, and at least one mounting platform 313a located towards the distal portion 312a of the elongated heat sink, for mounting at least one light source 313. These mounting platforms may be surfaces on the heat sink housing, as discussed before.

The heat sink 300 may also include at least one channel or valley, which may or may not run the length of the housing 301, as discussed above. A channel or valley (not shown) may also be present along the inner side wall 302b for wiring components.

The light sources 313 may be capable of emitting the same or different wavelengths. This heat sink construction may be capable of more effective heat dissipation by not concentrating the heat product at one location.

In one embodiment, each of the light sources 313 may include a light emitting diode (LED), or an LED array. Each of the LEDs (or LED arrays) emits light useful for initiating curing of a light activated material. In one embodiment, the combined light sources 313 may emit light of multiple wavelengths for activating a photoinitiator or multiple photoinitiators.

In one embodiment, the well 312 may accommodate the placement of LEDs 313 within the well and/or at the proximal portion 312b. Heat from the LEDs 313 may be conducted away by the housing 301. The side wall 320 of the well may be of a solid thermal conductive or metallic material. The material may be the same thermal conductive or metallic material as the rest of the housing 301, without a hollow interior. In another embodiment, the side wall 320 includes an inner side wall 320a and an outer side wall 320b surrounding a partially hollow interior of the well 312. This space may be filled with some phase change material 308 as well, or may provide expansion space for the phase change material 308 when it changes from one phase, occupying one space, into a phase occupying a larger space.

A capping device 303 may also be used to seal the hollow interior 307 at the open end 301b with an o-ring 309 and a formation 311 for a compression fit. A thermistor or other thermal sensor may be disposed in the channel 310 and fixed with a thermally conductive adhesive, such as those mentioned above, again to allow temperature information to be passed to a curing light control system. As discussed above, the capping device 303 may also be sealed with an adhesive to seal any pin holes that may exist. In other embodiments, pin holes or vent holes may be desirable to allow gas to escape. Again, to minimize any liquid phase change material 308 from escaping, a vapor impermeable/mositure permeable layer or film may be used to cover the holes.

Figure 7:
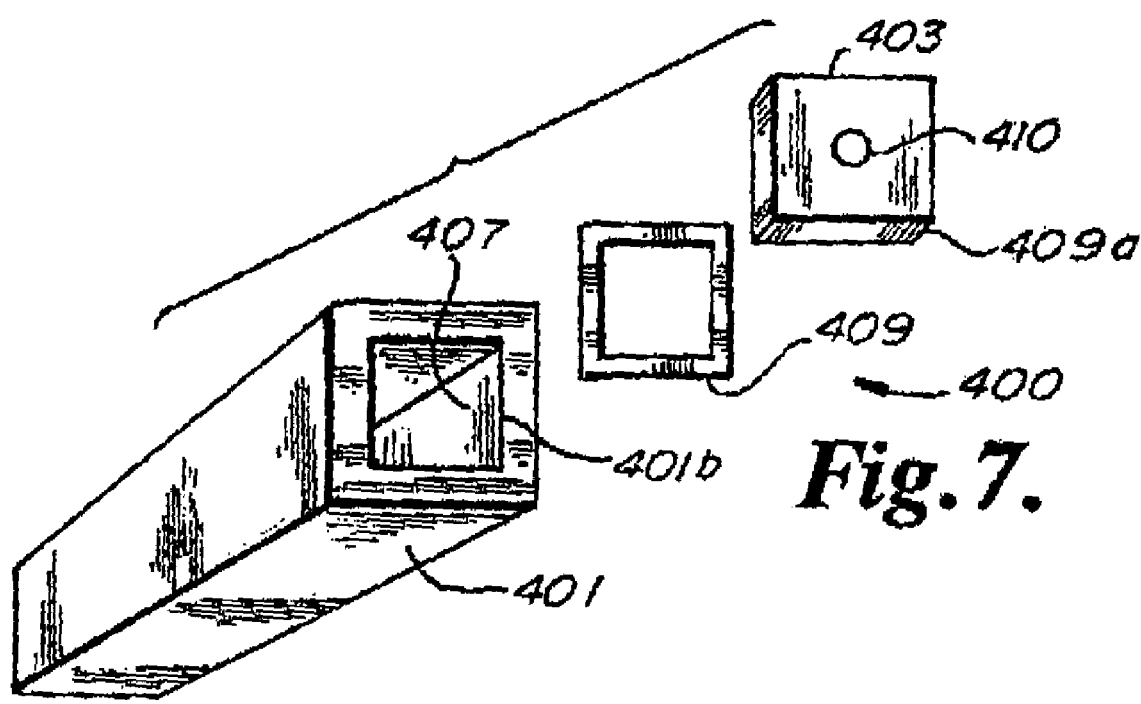
FIG. 7 shows an exploded perspective bottom side view of an embodiment of a heat sink of the present invention.

FIG. 7 shows another embodiment of a heat sink of the present invention. The heat sink 400 is of a square cross-section, having a housing 401, and a substantially hollow interior 402. The heat sink may be an elongated heat sink as shown, and the interior may either be of a substantially rectangular shape or a cylindrical shape.

This heat sink may be fitted again with a capping device 403, with a depression at the top of the capping device. An elastomeric gasket 409 may be again disposed about a channel 409a in the capping device.

The interior of the housing may also include a divider in one embodiment and no divider in another.

This heat sink may also be filled with a phase change material, as discussed above.

The gasket or o-ring may be made of any elastomeric or rubber material for providing a seal to minimize exposure of the phase change material to the environment outside of the housing.

In one embodiment, the housing may also have vent holes to allow the escape of gases, as mentioned above. In such embodiments, the recyclability of the heat sink may be reduced unless completely recyclable phase change materials are used. In one embodiment, these vent holes may also be covered with a vapor permeable, moisture impermeable layer, as mentioned above, surrounding the phase change material on the inside of the housing. In another embodiment, the vapor permeable, moisture impermeable layer may surround at least the portion of the housing having the vent holes on the outside of the housing. Examples of vapor permeable and moisture impermeable materials may include a water vapor permeable polyurethane film formed from a hot melt moisture curing adhesive containing at least one isocyanate functional polyurethane (which may be a reaction product of a component that contains NCO groups and a diol component with at least one linear dihydroxy polyester, formed from a diacid constituent and a diol constituent, the diol constituent may be a dihydroxy poplyether having a weight average molecular weight of at least 1000, and the ratio of OH:NCO in the isocyanate functional polyurethane is between 1.0:1.6 and 1.0:2.6) (disclosed in U.S. Pat. No. 5,851,661, the content of which is incorporated herein by reference) ; a film layer formed from a composition of a non-curing thermoplastic composition containing ethylene methacrylic acid copolymer or a polyether block amide, and at least one diluent such as a plasticizer (disclosed in U.S. Pat. No. 6,432,547, the content of which is incorporated herein by reference); a substrate with a thermoplastic composition made with a non-contact coating method to produce a substantially continuous coating of a variety of adhesives (such as polyethylene, polypropylene, copolymers of olefins, especially ethylene, and (meth-) acrylic acid; copolymers of olefins, such as ethylene, and (meth-) acrylic acid derivatives of (meth-) acrylic acid esters; copolymers of olefins, such as ethylene, and vinylic compounds of vinyl carboxylates such as vinyl acetate; thermoplastic rubbers (or synthetic rubbers) such as styrene-isoprene-styrene, styrene-butadiene-styrene, styrene-ethylene/butylene-styrene and styrene-ethylene/propylene-styrene block copolymers available in commerce under the tradenames of Kraton®, Solprene®, and Stereon®; metallocene-catalyzed polymers, especially based on ethylene and/or propylene; polyolefins such as ethylene, polypropylene and amorphous polyolefins (atactic poly-alpha-olefins) such as Vestoplast® 703 (Huls); polyesters; polyamides; ionomers and corresponding copolymers; and mixtures thereof), as disclosed in U.S. Pat. No. 6,843,874, the content of which is incorporated herein by reference; or similar.

Any embodiment of the heat sink described above may be constructed as a module so that it may be changed or exchanged when needed.

The embodiments of heat sink described above may be used in a curing light system. The curing light may be a hand-held portable curing light system operated by batteries or a chair side curing light system operated by AC power. A heat sink including a phase change material may be installed in the curing light or a photobleaching light device in the same manner a conventional metal block heat sink is installed. As mentioned above, some curing lights and photobleaching lights are generally supported when in use, therefore the weight of the device is not as problematic. However, a more efficient heat sink may be beneficial and can nevertheless lead to the construction of a more compact bleaching light.

The heat sink including at least one phase change material may be used by itself or in conjunction with a conventional metal heat sink or a fan. In the case of a light source used in whitening teeth, an additional cooling system such as a liquid coolant may also be used.

Figure 8:
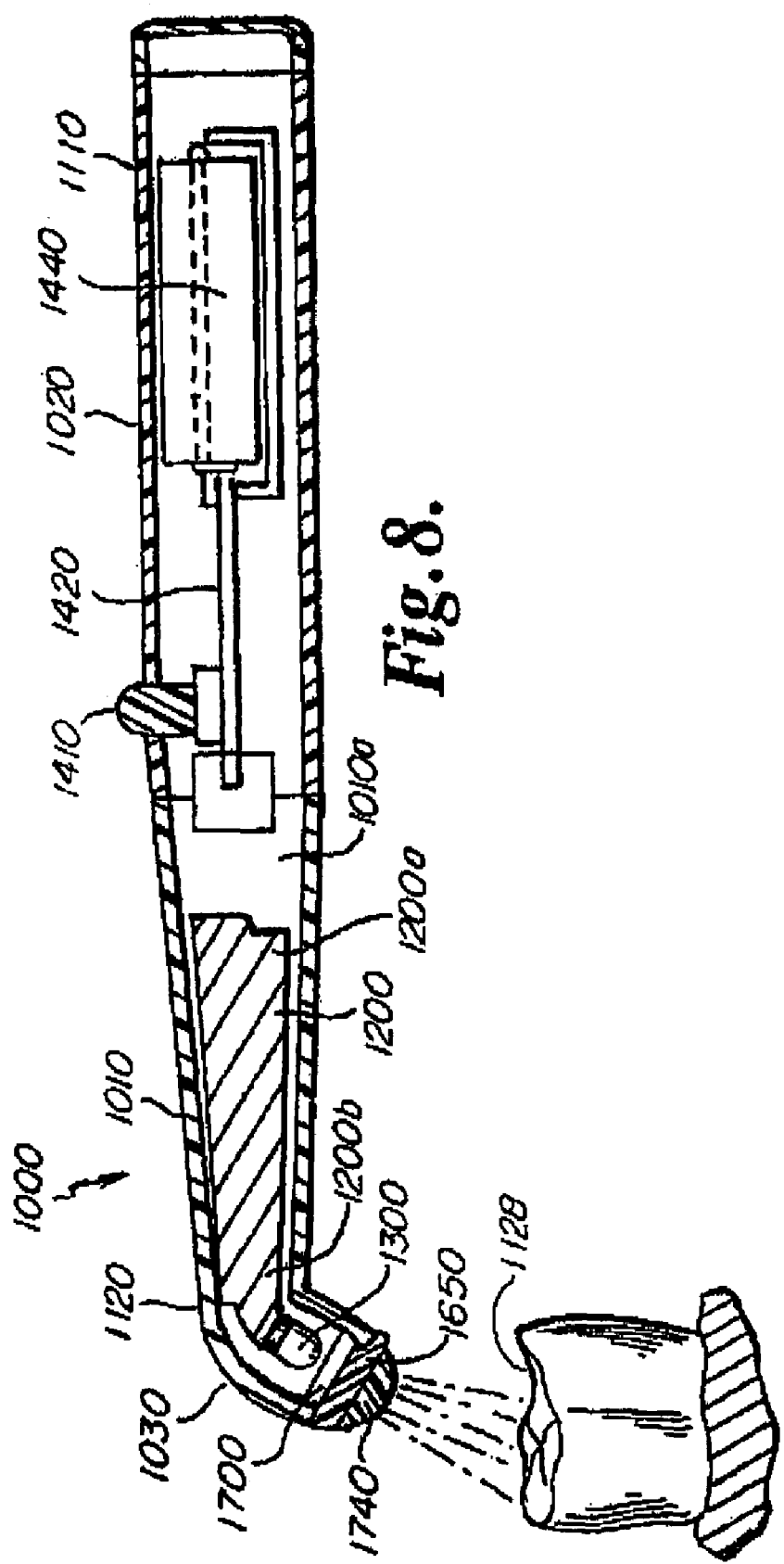
FIG. 8 shows a cross-sectional view of a curing light according to one embodiment of the invention.

FIG. 8 shows an embodiment of a curing light 1000 of the present invention, having a light module housing 1010 including a distal end 1110, a proximal end 1120, a handle 1020 towards its distal end and a neck and head portion or body 1030 on its proximal end at an angle to the handle portion 1020. The light module housing 1010 has a substantially cylindrical shape having a substantially hollow interior 1010a with at least one heat sink 1200 located in the light module housing 1010. The heat sink 1200 may have a longitudinal axis, or may be of any configuration adapted to promote effective thermal management within the curing light 1000. In one embodiment the head and neck portion 1030 may also include a light guide, such as the internal light guide 1700 shown here in FIG. 8. In other embodiments, the curing light may include an external light guide.

In some embodiments, a lens cover 1650 may be located towards the proximal end 1120 of the light module housing 1010, as shown. In one embodiment, the lens cover 1650 may be a transparent window through which light travels before striking a composite material or surface to be cured or whitening material 1128 to be acted on. Some examples of the housings include sealed plastic and sealed metal ends with a window.

In other embodiments, the cover 1650 may be a focusing device, which may include a focusing lens or dome 1740 for focusing the light towards a target surface 1128. In another embodiment, the housing 1010 may have a focusing dome 1740 integrally bonded to or formed or molded with the housing, to focus light emitted by the laser diodes or the light emitting diodes before delivering it to a remote location. Thus, the housing may be constructed therefore not only to serve to protect the light source, but also serve to focus light.

The focusing dome or lens 1740 may also act as a device for modifying the footprint or varying the diameter of the light beam exiting the proximal end 1120 of the housing 1010, in order to more correctly direct the beam of light, either at a smaller target area or over a wider target area. The light module housing 1010 also houses and protects, for example, electronic circuits 1420 and a DC battery pack 1440.

Referring again to FIG. 8, one embodiment includes an elongated heat sink 1200 having a distal end 1200a and a proximal end 1200b. The heat sink 1200 may be located in the light module housing 1010 with the proximal end 1200b being situated closer to the proximal end 1120 of the housing 1010. The heat sink 1200 may also be in any other shape. At least one mounting platform (not shown) or simply a surface may be located at the distal end 1200a, and at the proximal end 1200b of the elongated heat sink 1200. When other shapes of the heat sink 1200 are included in the invention, the mounting platforms may be located at the proximal or distal surface or portion.

Mounted on each of the mounting platforms or surfaces is a light source 1300. The light source 1300 is, for example, an LED or an LED array. In one embodiment, the light sources 1300 may be located towards the proximal end 1120 of the housing 1010, so that they are close to the target area. In another embodiment, the device is fitted with a light guide 1700 to keep one or more of the light sources away from the target. The light guide 1700 here may be an extension of the housing 1010.

In some embodiments, the chips of the light source 1300, when used, may be collectively located on a single heat sink 1200 for heat dissipation or individually seated to its own heat sink. In some embodiments, the light source 1300 may be seated on a larger heat sink 1200 with electrode channels.

Also, in some embodiments, when chips are used, the heat sink 1200 including phase change material of the present invention may be in direct or indirect contact with the light emitting chip or chips 1300. After the phase change material absorbs the heat generated by the chips 1300, heat may then be dissipated. A conventional metal heat sink may be mounted adjacent to the heat sink 1200 of the present invention including at least one phase change material, either beside or beneath it. A fan may also be provided in lieu or in addition to the conventional metal heat sink.

In one embodiment, single or multiple LED chips or laser diode chips 1300 may be located on a conventional metal block heat sink, which directly absorbs heat generated by the light source or sources 1300, and the heat sink 1200 including at least one of the phase change material absorbs the heat coming from the thermally conductive or metal block. The heat sink 1200 including at least one phase change material may dissipate heat coming from the thermally conductive or metal block by being mounted adjacent to, either beside, or beneath the conventional metal block heat sink.

In another embodiment, the chips of the light source 1300 are either collectively located on a single heat sink 1200 including phase change material for heat dissipation or individually seated to its own heat sink 1200' including phase change material.

In other embodiments of the invention, a light source 1300 including LED's or laser diode chips may be located on a face of the heat sink 1200 and around the periphery of that face of the heat sink. In this configuration, more LED's or laser diode chips 1300 be placed on the heat sink 1200 either to achieve a more powerful light or to accommodate the necessary number of wavelengths of light that are desired to be produced.

In addition, electrodes providing power to the laser or the LED chips 1300 may also be included in the housing 1010.

At the beginning of operation, the phase change material may be, for example, in a solid state at ambient temperature, although a liquid may also be used if special provisions are made for containing the gas produced during phase change. As heat is generated by the light source or sources, it is conducted away by the thermally conductive or metal casing or metal wall and absorbed by the phase change material. The solid or liquid absorbs heat from the casing and undergoes a phase change to a liquid or gas, respectively. Some sublimation may also be happening. When a substantial proportion of the material has undergone phase change to a new state or phase, an internal thermal sensor may be provided to effect the shut off of the curing light or bleaching light at a given temperature. After reaching this shut off temperature, the liquefied or gasified phase change material then begins to dissipate heat, when the thermally conductive or metal casing is removed from any heat generating source, for example, the light source is turned off. This heat dissipation is again through the thermally conductive or metal casing, in an attempt by the phase change material to return to its initial state of solid or liquid, respectively. When most of the phase change material comes substantially close to ambient temperature, it will then remain a solid or liquid until it once again experiences a rise in temperature to its melting or gasifying point and the process is repeated. Since the phase change material undergoes substantially reversible phase changes, it may typically go through a large, if not an infinite number of cycles without losing its effectiveness.

In one embodiment, the light from the light source 1300 exits the housing 1010 and travels directly to a curing surface 1128 without first going through a light guide or fiber optic 1700. In other embodiments, the light travels from the light source 1300 to a curing surface 1128 by first going through a light guide or fiber optic 1700.

The light source 1300 may be, for example, located in a handle that may be manipulated by a user in order to direct light emitted by the light source 1300 to composite materials 1128 to be cured. In some embodiments, at least a portion of handle is flexible that may be bent in any desired direction for ease of use. The flexible portion includes at least a soft protective material surrounding at least one bendable wire.

The heat coming out of the housing may be dissipated by a heat sink 1300 including the phase change material, a conventional metal block, or a fan, located in the handle, or just by ambient air.

As discussed before, when multiple light sources 1300 are used, they may emit multiple wavelengths of light so that composite materials having photoinitiators sensitive to different wavelengths may all be cured with a single light source 1300. In some embodiments, diode lasers or light emitting diodes 1300 may be arranged in an array on an appropriate base or fixture in order to provide greater light power or to provide a varying diameter light source 1300 if a concentric array is used. Further, when an array of laser or light emitting diode chips 1300 is used, a light having single or multiple wavelengths may be achieved by placing the chips 1300 with different wavelength in the array.

Furthermore, the curing or photobleaching light system may be equipped with a control module with AC or DC power 1440. The control module powers and controls the curing or photobleaching light system so that appropriate light for curing a composite material or for bleaching a photoactive bleaching composition is provided at a desired light intensity for any desired time duration. An on/off switch and an indicator 1410 for low battery power can also be provided.

In some embodiments of the invention a battery charger is provided for charging one or more batteries used to power the light source 1300. When the battery is being charged, the curing or photobleaching light may still be used for treatment because power can be drawn from the charger to power the curing light.

The present invention is further exemplified in the following example:

EXAMPLE

A heat sink embedded in a dental curing light was constructed as follows:

Composition and property of phase change material used:
Phase change material (PCM): Sodium Hydrogen Phosphate Dodecahydrate ($Na_2HPO_4.12H_2O$) having the following properties was used:
Melting Point: 36° C.
Heat of Fusion: 280 kj/kg
Specific Heat: 1.94 kJ/kg° C. (solid), 1.60 kJ/kg° C. (liquid)
Density: 1520 kg/m3 (solid), 1450 kg/m3 (liquid)
Thermal Conductivity: 0.514 W/m° C. (solid), 0.476 W/m° C. (liquid)

The thermally conductive housing: a copper casing (tellurium copper 145), having wall thickness of about 1.5 mm.

Preparation:
The phase change material was heated for 45 minutes at 55° C. in an oven until melted. 1.2 mL of phase change material in liquid phase was loaded into the hollow copper casing of the heat sink using a syringe. The heat sink was cooled with a fan for 30 minutes before a cap was pressed into place to seal the chamber. A thermistor was placed into the channel of the cap and sealed into place with thermal epoxy. Additional thermal epoxy was also applied to the interior of the cap to provide further sealing.

Test:
The constructed heat sink of the above specified configuration was tested in a curing light in accordance with the present invention. The testing consisted of determining the run-time of the curing light when utilizing a heat sink including a phase change material in comparison to a heat sink without a phase change material. Run-time testing determined the operational time prior to the curing light shut-off temperature. A rise of temperature to 40° C. from an ambient temperature of 25° C. was obtained. The curing light employing a heat sink including a phase change material averaged a run-time of greater than 20 minutes (a total of 20 samples with approximately the same construction was run) and the curing light employing a comparable heat sink except without a phase change material averaged a run-time of about 8 minutes (a total of 67 samples were run).

The heat sink of the present invention demonstrated a superior performance when compared to conventional solid metal block heat sinks, even at a lower weight.

Although the present invention has been described in detail with respect to some embodiments, it will be appreciated by those of ordinary skill in the art that the invention can also be embodied in other forms without departing from the spirit or essential character hereof. The present description is therefore considered in all respects to be illustrative and not restrictive. The scope of the present invention is indicated by the appended claims, and all changes that come within the meaning and range of equivalents thereof are intended to be embraced therein.

The invention claimed is:

1. A light weight, hand held curing light system useful for curing light activated composite materials comprises:

a light source housing comprising at least one light source mounted on at least one heat sink for drawing heat away from said at least one light source, said at least one heat sink comprising:

a thermally conductive housing having an open end, a closed end, and a substantially hollow interior, said thermally conductive housing is substantially contained in the light source housing;

a capping device comprising a formation for compression fitting in the open end of the thermally conductive housing; and at least one phase change material, undergoes substantially reversible phase changes, that partially fills said conductive housing; and said at least one light source mounted on the closed end of said thermally conductive housing;

wherein said curing light system has a power supply locatable on said light source housing, said power supply serving to provide electrical power to said light source.

2. The curing light system of claim 1 wherein at least one well is located on said closed end of said at least one heat sink, said well being sized and shaped to accommodate a light emitting diode.

3. The curing light system of claim 2 wherein said well has an annular wall, serving to reflect light in a desired direction.

4. The curing light system of claim 3 wherein said well comprises a side wall having an inner side wall and an outer side wall, and a substantially hollow space between said inner side wall and said outer side wall.

5. The curing light of claim 3 wherein said well having at least one side wall, two proximal portions at the top of the well and a distal portion at the bottom of the well, the portions being adapted for mounting at least one light source.

6. The curing light system of claim 1 wherein said light source housing comprises:

a body located about the exterior of said light source, said body serving to contain said light source;

a light exit located on said body; and a cover covering said light exit, said cover permitting light emitted from said light source to pass through said light exit and travel to a curing surface.

7. The curing light system of claim 1 wherein said phase change material is selected from a group consisting of organic materials, inorganic materials and combinations thereof.

8. The curing light system of claim 1 wherein said phase change material has a melting point between about 35 to 45 degrees C.

9. The curing light system of claim 1 wherein said phase change material has a specific heat of more than about 1.7 at ambient temperature.

10. The curing light system of claim 1 wherein said phase change material has a specific heat of more than about 1.5 at elevated temperatures.

11. The curing light system of claim 1 wherein said phase change material has a thermal conductivity of at least about 0.5 W/m0C at ambient temperature.

12. The curing light system of claim 1 wherein said phase change material has a thermal conductivity of at least about 0.45 W/m0C at elevated temperatures.

13. The curing light system of claim 1 wherein the curing light system has a longer average run time when compared to a curing light system having the same light source and a heat sink of substantially equivalent volume without the phase change material.

14. The curing light system of claim 1 comprising a plurality of light emitting chips, at least some of said chips for emitting light of a wavelength different from that emitted by others of said chips.

15. The curing light of claim 1 further comprising a light transport apparatus.

16. A light weight, handheld curing light system comprises a light source housing comprising at least one light source mounted on at least one heat sink for drawing heat away from said at least one light source, said at least one heat sink comprising:
 a thermally conductive housing substantially contained inside the light source housing, said conductive housing comprising an open end, a closed end, and a substantially hollow interior; and
 a capping device comprising a formation for fitting in the open end of the thermally conductive housing;
 wherein said substantially hollow interior of said thermally conductive housing is partially filled with at least one phase change material for absorbing heat generated by the light source mounted on the closed end of said conductive housing;
 wherein said curing light system has an average longer run time when compared to a curing light system having a heat sink with a substantially equivalent volume that does not contain a phase change material.

17. The light system of claim 16 wherein said phase change material is selected from a group consisting of organic materials, inorganic materials and combinations thereof.

18. The light system of claim 17 wherein said organic phase change material is selected from the group consisting of paraffin waxes, 2,2-dimethyl-n-docosane (C24H50), trimyristin, ((C13H27COO)3C3H3), 1,3-methyl pentacosane (C26H54), polyethylene waxes, ethylene-bis-stearamide, N,N-ethylene-bis-stearamide, and mixtures thereof.

19. The light system of claim 17 wherein said inorganic phase change material comprises inorganic hydrated salts.

20. The light system of claim 17 wherein said inorganic phase change material is selected from the group consisting of sodium hydrogen phosphate dodecahydrate (Na2HPO4.12 H2O), sodium sulfate decahydrate (Na2SO4.10H20), ferric chloride hexahydrate (FeCl3.6 H20), TH29, metallic alloys and mixtures thereof.

21. The light system of claim 16 wherein said phase change material is a solid at ambient temperature.

22. The light system of claim 16 wherein said phase change material has a melting point between about 30 to about 50 degrees C.

23. The light system of claim 16 wherein said phase change material has a melting point between about 35 to 45 degrees C.

24. The light system of claim 16 wherein said phase change material has a specific heat of more than about 1.7 at ambient temperature.

25. The light system of claim 16 wherein said phase change material has a specific heat of more than about 1.5 at elevated temperatures.

26. The light system of claim 16 wherein said phase change material has a thermal conductivity of at least about 0.5 W/m0C at ambient temperature.

27. The light system of claim 16 wherein said phase change material has a thermal conductivity of at least about 0.45 W/m0C at elevated temperatures.

28. The light system of claim 16 wherein said housing comprises a blade-like divider for partitioning the substantially hollow interior.

29. The light system of claim 16 wherein said thermally conductive housing comprises an interface feature comprising a substantially flat surface adapted for mounting a light source.

30. The light system of claim 16 wherein said phase change material is substantially surrounded by a vapor permeable and moisture impermeable film.

31. The light system of claim 16 wherein said thermally conductive housing comprises vent holes.

32. The light system of claim 31 wherein at least a portion of the housing comprising the vent holes is substantially surrounded by a vapor permeable and moisture impermeable film.

33. The light system of claim 16 wherein said thermally conductive housing comprises a cylindrical or a rectangular cross-section.

34. The light system of claim 16 wherein said thermally conductive housing comprises at least one channel running along the outside wall of the housing, said channel is adapted for position wiring components.

35. The light system of claim 16 wherein said thermally conductive housing comprises a substantially centrally located deep well having at least one side wall, two proximal portions a the top of the well and a distal portion at the well, the portions being adapted for mounting at least one light source.

36. The light system of claim 35 wherein said side wall comprises a solid thermally conductive material.

37. The light system of claim 35 wherein said side wall comprises an inner side wall and outer side wall with a substantially hollow space between the inner and outer side walls.

38. The light system of claim 16 wherein said phase change material has a latent heat of fusion of at least about 30 kJ/kg.

39. The light system of claim 38 wherein said phase change material has a latent heat of fusion of at least about 200 kJ/kg.

40. A light weight photocuring or photobleaching light system comprising:
 a light source housing comprising at least one light source mounted on at least one heat sink for drawing heat away from said at least one light source, said at least one heat sink comprising:
 a thermally conductive block substantially contained in the light source housing, said thermally conductive block having a bore, said bore being at least partially filled with at least one phase change material undergoing substantially reversible phase changes, and
 a capping device for capping and open end of said block for containing said phase change material inside said bore;
 wherein said light source is mounted on said block away from said open end
 wherein said photocuring or photobleaching light system has a power supply locatable on said light source housing, said power supply serving to provide electrical power to said light source.

41. The light system of claim 40 wherein said phase change material is selected from a group consisting of organic materials, inorganic materials and combinations thereof.

42. The light system of claim 40 wherein said phase change material has a melting point between about 30 to 50 degrees C.

43. The light system material of claim 40 wherein said phase change material has a specific heat of more than about 1.7 at ambient temperature.

44. The light system of claim 40 wherein said phase change material has a specific heat of more than about 1.5 at elevated temperatures.

45. The light system of claim 40 wherein said phase change material has a thermal conductivity of at least about 0.5 W/m0C at ambient temperature.

46. The light system of claim 40 wherein said phase change material has a thermal conductivity of at least about 0.45 W/m0C at elevated temperatures.

47. The light system of claim 40 wherein said phase change material is substantially surrounded by a vapor permeable and moisture impermeable film.

48. The light system of claim 40 wherein said block comprises vent holes.

49. The light system of claim 48 wherein at least a portion of the block comprising the vent holes is substantially surrounded by a vapor permeable and moisture impermeable film.

50. The light system of claim 40 wherein said block comprises at least one channel running along the outside wall of the block, said channel is adapted for positioning wiring components.

51. The light system of claim 40 wherein said block comprises a substantially centrally located deep well having at least one side wall, two proximal portions at the top of the well and a distal portion at the bottom of the well, the portions being adapted for mounting at least one light source.

52. The light system of claim 51 wherein said side wall comprises a solid thermally conductive material.

53. The light system of claim 51 wherein said side wall comprises an inner side wall and outer side wall with a substantially hollow space between the inner and outer side walls.

54. The light system of claim 40 wherein said phase change material has a latent heat of fusion of at least about 30 kJ/kg.

55. The light system of claim 54 wherein said phase change material has a latent heat of fusion of at least about 2000 kJ/kg.

* * * * *